(12) United States Patent
Davankov

(10) Patent No.: US 6,408,894 B1
(45) Date of Patent: Jun. 25, 2002

(54) METHOD OF PRODUCING DEVICES FOR BLOOD PURIFICATION

(75) Inventor: Vadim Davankov, Moscow (RU)

(73) Assignee: RenalTech International, LLC, New York, NY (US)

(*) Notice: Subject to any disclaimer, the term of this patent is extended or adjusted under 35 U.S.C. 154(b) by 0 days.

(21) Appl. No.: 09/840,890

(22) Filed: Apr. 25, 2001

(51) Int. Cl.⁷ .................................................. B65B 1/20
(52) U.S. Cl. ............................ 141/12; 141/7; 210/767
(58) Field of Search ........................... 141/11, 12, 69, 141/71, 73, 80; 210/654, 767

(56) References Cited

U.S. PATENT DOCUMENTS 4,483,374 A * 11/1984 Siemion ........................ 141/9
5,407,581 A * 4/1995 Onodera et al. ............ 210/654

* cited by examiner

Primary Examiner—Gregory L. Huson
Assistant Examiner—Peter deVore
(74) Attorney, Agent, or Firm—I. Zborovsky

(57) ABSTRACT

A method of producing a device for purifying blood from toxins includes providing a container with an inlet and outlet, preparing a mixture of a porous beaded adsorbent polymeric material with a liquid, and supplying the mixture under the pressure through the inlet into the interior of the container so that liquid is squeezed out of the mixture and leaves the container through the outlet, while the beads of the beaded polymeric material are homogeneously and densely packed in an interior of the container.

9 Claims, 1 Drawing Sheet

METHOD OF PRODUCING DEVICES FOR BLOOD PURIFICATION

BACKGROUND OF THE INVENTION

The present invention relates to a method of producing devices for blood purification.

It is known that in order to purify the blood, for example for patients having kidney problems, or for patients who have been infected and are endangered by sepsis, blood is withdrawn from a patient and then purified by passing through a purifying material, such as for example an adsorbing polymer, and then the blood from which toxins are removed completely or at least partially is introduced again into the patient. For this blood purification, corresponding blood purification devices are utilized, which are formed usually as containers or cartridges filled with the adsorbing polymer, for example a polymer composed of porous beads with pores selected so as to remove toxins from blood. These known devices are made by first forming a container, and then introducing the beaded adsorbing polymeric material into them. In accordance with the existing practice, a container is first filled with a liquid and then beads are introduced through the inlet of the container into the liquid. It has been found that such a method does not provide a uniform distribution and dense packing of the beads inside the container and filling the container cannot be performed with a high speed.

SUMMARY OF THE INVENTION

Accordingly, it is an object of the present invention to provide method of producing devices for blood purification, which avoids the disadvantages of the prior art.

In keeping with these objects and with others which will become apparent hereinafter, one feature of present invention resides, briefly stated, in a method of producing devices for blood purification, in accordance with which a container for accommodating a beaded adsorbent polymeric material is provided, a mixture of a beaded polymeric material with a liquid is formed (a slurry), and then the thusly formed mixture of the beaded polymeric material with the liquid is introduced under pressure into the container so that the beads of the polymeric material are densely packed in the interior of the container while the liquid of the mixture leaves through an outlet of the container.

When the method is performed in accordance with the present invention, the container is filled with the beaded polymeric material very fast, preferably in an easily automated manner, and at the same time homogenous and dense packing of the beaded polymeric material inside the container is provided.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

The single figure of the drawing is a view illustrating method of producing devices for blood purification in accordance with the present invention.

DESCRIPTION OF THE PREFERRED EMBODIMENTS

Figure 1:
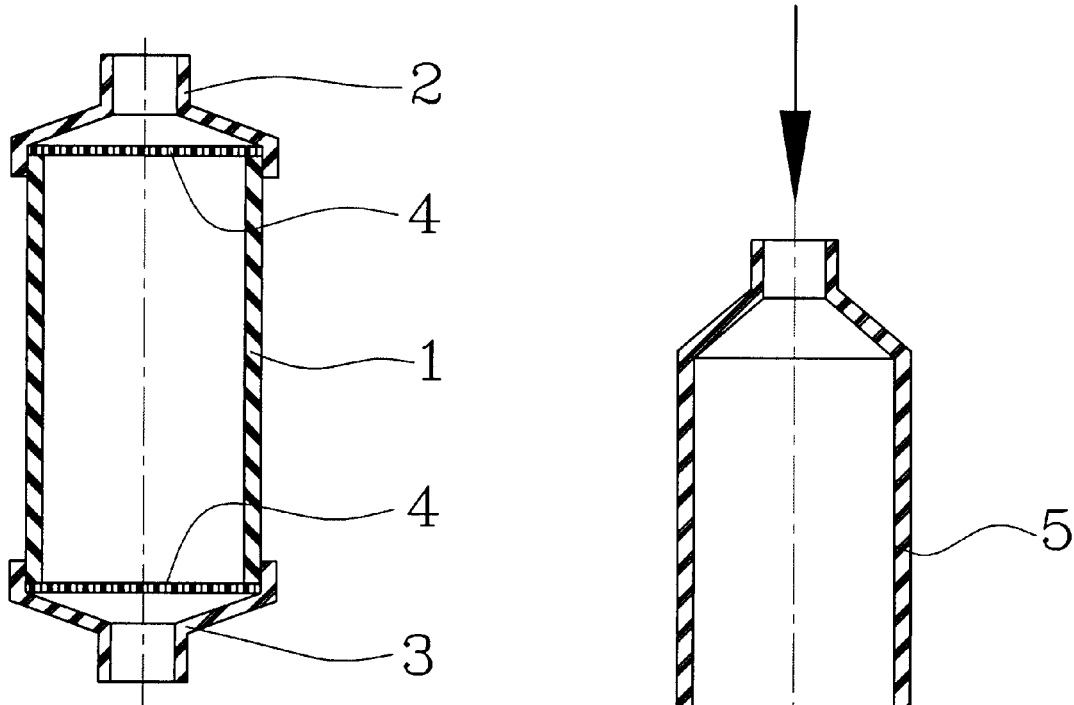
Figure 2:
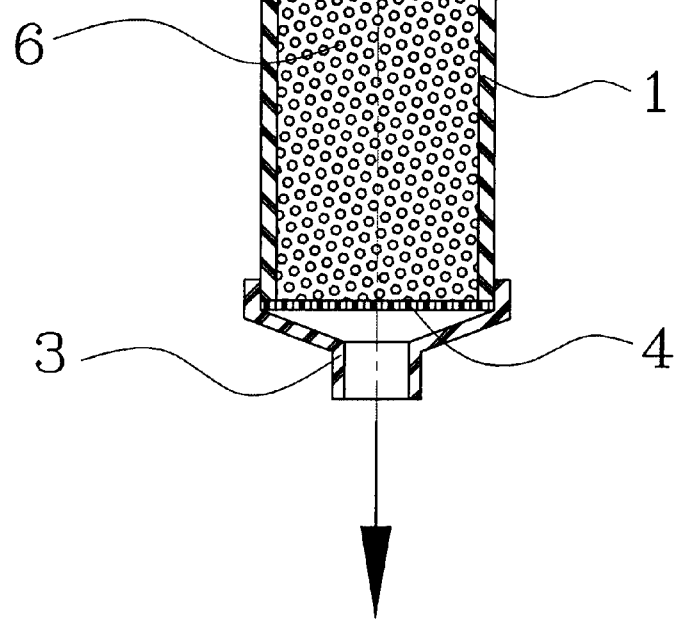

In order to make a blood purification device, first a container 1 is provided which has an inlet 2 and an outlet 3, both openable and closeable when needed. The space occupied by the adsorbing material is separated from the inlet and outlet parts of the device by means of a screen or a mesh 4 which openings are smaller than the size of the adsorbent particles and which prevents the adsorbent particles from escaping the device and contaminating the purified blood.

A mixture of a beaded adsorbent polymeric material, for example porous styrene/divinylbenzene beads with a hemocompatible coating, with an aqueous solution, for example water or physiological saline is produced. The homogeneous slurry is formed by a known mixing processes in a mixing device such as for example glass or polymeric vessel, in which desired amounts of the components of the mixture are introduced and thoroughly mixed by a stirrer or by gentle shaking the vessel as a whole.

The thusly prepared mixture is then forcedly introduced, for example under pressure into the interior of container 1. For this purpose the inlet part 2 is removed and replaced by an open filling device 5. The outlet 3 remains open as well. It is provided with a screen 4 which allows discharge of liquid but prevents discharge of beads of the beaded adsorbent polymeric material from the container. The pressure which is utilized for supplying the mixture into the container 1 is for example within the range of 0.1 to 10 bar, preferably between 0.1 and 5 bar. Another option is applying vacuum (suction) at the outlet 3. In this case the pressure drop over the device during the packing procedure remains within the limits between 0.1 and 1.0 bar.

During the process of filling the container 1 with the mixture, liquid is expelled from the mixture under the action of supplying of subsequent quantities of the mixture or under the suction of vacuum, and leaves the container through the outlet 3. The beads 6 of the beaded adsorbent polymeric material are homogeneously and densely packed in the interior of the container, one layer after the other. As a result the container is filled with the beaded adsorbent polymeric material uniformly and tightly with a high speed.

Next, the filling device has to be replaced with the inlet part 2 with the mesh 4 inserted on the top of the packed bed of the polymeric beads. A particular problem in this operation is that no particles and no liquid remain in the filling device 5 and on the top of the packed polymeric bed. Otherwise, beads would hinder the tight sealing of the inlet piece on the housing 1 or crush and produce fines during the sealing. This is prevented by flashing the packed bed with air or carbon dioxide, prior to removing the filling device 5.

With the inlet piece 2 positioned on the housing 1 and the adsorption device thus assembled and sealed, the gas inside the device option is applying vacuum (suction) at the outlet 3. In this case the pressure drop over the device during the packing procedure remains within the limits between 0.1 and 1.0 bar.

During the process of filling the container 1 with the mixture, liquid is expelled from the mixture under the action of supplying of subsequent quantities of the mixture or under the suction of vacuum, and leaves the container through the outlet 3. The beads 6 of the beaded adsorbent polymeric material are homogeneously and densely packed in the interior of the container, one layer after the other. As a result the container is filled with the beaded adsorbent polymeric material uniformly and tightly with a high speed.

Next, the filling device has to be replaced with the inlet part 2 with the mesh 4 inserted on the top of the packed bed of the polymeric beads. A particular problem in this operation is that no particles and no liquid remain in the filling device 5 and on the top of the packed polymeric bed.

Otherwise, beads would hinder the tight sealing of the inlet piece on the housing 1 or crush and produce fines during the sealing. This is prevented by flashing the packed bed with air or carbon dioxide, prior to removing the filling device 5.

With the inlet piece 2 positioned on the housing 1 and the adsorption device thus assembled and sealed, the gas inside the device that is situated between the adsorbent beads has to be completely replaced with water or saline. This is achieved by flashing the device with carbon dioxide and replacing it with an aqueous media that easily dissolves carbon dioxide.

Water dissolves high amounts of carbon dioxide under enhanced pressures. Therefore, the assembled device is flashed with water or physiological saline under excessive pressure of 0.1 to 5.0 bar. Another option is flashing the device first with a solution of sodium carbonate or sodium hydroxide and then with water or saline. In this case, no exccessive pressure is needed, since the above alkaline solutions quickly dissolve carbon dioxide remaining between the polymer particles of the tightly packed bed. It is obvious that the liquid intended to dissolve and replace carbon dioxide between the polymer particles should be introduced into the packed device from the lower outlet part 3 of the device. In this case, major part of carbon dioxide will be simply displaced from the device and the remaining amount of carbon dioxide to be dissolved remains minimal. This would minimize the amount of pressurized water or soda solution needed for final flashing the device prior to sealing the inlet and out et openings 2 and 3.

All the above procedures of packing the device under pressure, flashing it with carbon dioxide and pressurizsed aqueous solutions are very fast and can be easily automated.

It will be understood that each of the elements described above, or two or more together, may also find a useful application in other types of constructions differing from the types described above.

While the invention has been illustrated and described as embodied in method of producing devices for blood purification, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:

1. A method of producing a device for purifying blood from toxins, comprising the steps of providing a container with an inlet and an outlet; preparing a mixture of a porous beaded adsorbent polymeric material with a liquid; and supplying the mixture forcedly through said inlet into an interior of said container so that the liquid is squeezed out of the mixture and leaves the container through said outlet, while porous beads of the beaded polymeric material are homogeneously and densely packed in an interior of the container.

2. A method as defined in claim 1, wherein said supplying is performed under the action of pressure at an inlet side of the container.

3. A method as defined in claim 1, wherein said forced supplying is performed under the action of suction at an outlet side of the container.

4. A method as defined in claim 1; and further comprising the step of leaving said outlet open during filling of the mixture, so as to allow the liquid to escape through said outlet.

5. A method as defined in claim 4; and further comprising providing a screen upstream of said outlet so as to allow passage of the liquid through said screen and thereafter through said outlet and to prevent escape of the beads of the beaded adsorbing polymeric material.

6. A method as defined in claim 1; and further comprising flashing the packed material in the interior of the container.

7. A method as defined in claim 6, wherein said flashing includes introducing into the container a flashing gaseous medium to be situated between the beads, and subsequently replacing the flashing gaseous medium with an aqueous medium.

8. A method as defined in claim 7, wherein said flashing gaseous medium is carbon dioxide.

9. A method as defined in claim 7, wherein said aqueous medium is a medium selected from the group consisting of pressurized water, saline and aqueous solutions of sodium carbonate or sodium hydroxide.

* * * * *